US012709587B2

(12) United States Patent
Jeroro et al.

(10) Patent No.: US 12,709,587 B2
(45) Date of Patent: Aug. 18, 2026

(54) PROCESS FOR CONVERTING OXYGENATES TO DISTILLATE FUELS

(71) Applicant: UOP LLC, Des Plaines, IL (US)

(72) Inventors: Eseoghene Jeroro, Chicago, IL (US); Manuela Serban, Northbrook, IL (US)

(73) Assignee: UOP LLC, Rosemont, IL (US)

( * ) Notice: Subject to any disclaimer, the term of this patent is extended or adjusted under 35 U.S.C. 154(b) by 181 days.

(21) Appl. No.: 18/393,364

(22) Filed: Dec. 21, 2023

(65) Prior Publication Data

US 2025/0206682 A1 Jun. 26, 2025

(51) Int. Cl.

*C07C 2/24* (2006.01)
*B01J 21/12* (2006.01)
*B01J 23/755* (2006.01)
*C07C 1/24* (2006.01)
*C07C 5/03* (2006.01)

(52) U.S. Cl.

CPC ................ *C07C 2/24* (2013.01); *B01J 21/12* (2013.01); *B01J 23/755* (2013.01); *C07C 1/24* (2013.01); *C07C 5/03* (2013.01); *C07C 2521/12* (2013.01); *C07C 2523/755* (2013.01)

(58) Field of Classification Search

CPC .... C07C 2/24; C07C 1/24; C07C 5/03; C07C 2521/12; C07C 2523/755; C07C 2529/40; C07C 2529/70; C07C 1/20; B01J 21/12; B01J 23/755; C10G 1/00
USPC .......................................................... 585/255
See application file for complete search history.

(56) References Cited

U.S. PATENT DOCUMENTS 5,258,570 A * 11/1993 Skeels .................. B01J 29/7415 208/46
2016/0194572 A1* 7/2016 Lilga ......................... C07C 2/24 585/277

* cited by examiner

*Primary Examiner* — Prem C Singh
*Assistant Examiner* — Francis C Campanell
(74) *Attorney, Agent, or Firm* — Paschall & Associates, LLC; Mark Goldberg; James C. Paschall

(57) ABSTRACT

A process is provided to produce increased amounts of cycloparaffin compounds in a methanol to jet fuel process by modifying the olefin oligomerization step that after hydrogenation provides the increased quantities of cycloparaffins for jet fuel. A two stage oligomerization process is employed in which an acidic catalyst such as a zeolite is in one reactor and a metal, such as nickel, on alumina catalyst is in a second reactor. The two stages may be in either order in the process. A small amount of aromatic compounds may be added to the feed to achieve the desired level of cycloparaffins in the product. Adjustments to other aspects of the process may also help to provide a product with higher cycloparaffin content.

16 Claims, 1 Drawing Sheet

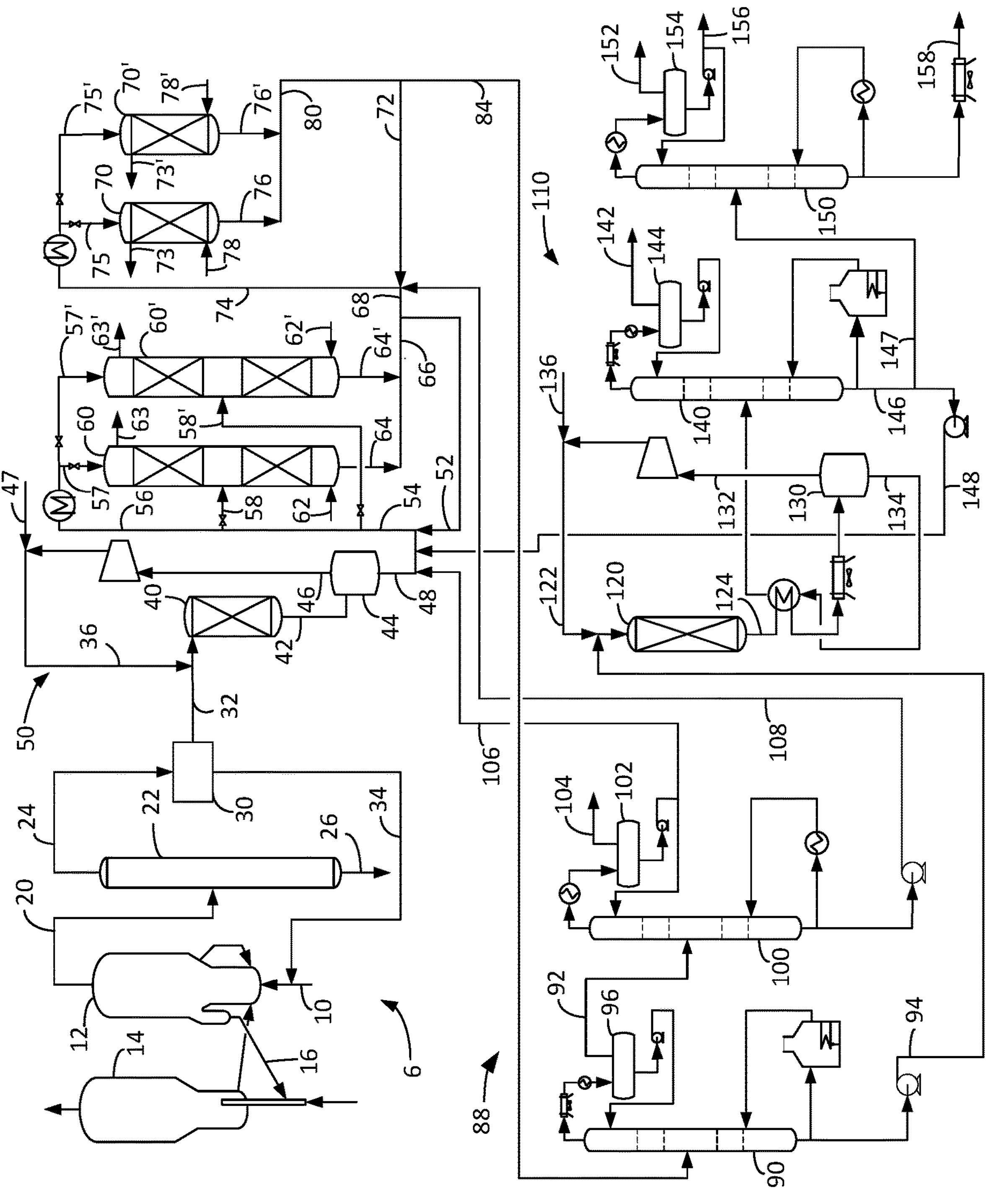

PROCESS FOR CONVERTING OXYGENATES TO DISTILLATE FUELS

FIELD

The field is the conversion of oxygenates to distillates. In particular, the field may particularly relate to production of distillates having a higher concentration of cycloparaffin compounds for use in jet fuels.

BACKGROUND

Carbon dioxide is a so-called greenhouse gas for which many desire to reduce the concentration in the atmosphere. Carbon dioxide may be converted to oxygenates such as methanol or dimethyl ether. Molecular sieves such as microporous crystalline zeolite and non-zeolitic catalysts, particularly silicoaluminophosphates (SAPO), are known to promote the conversion of oxygenates to hydrocarbon mixtures, particularly hydrocarbon mixtures composed largely of light olefins. The highly efficient Methanol to Olefin (MTO) process may convert oxygenates to light olefins which had been typically considered for plastics production. Light olefins produced from the MTO process is highly concentrated in ethylene and propylene.

Light olefin dimerization and oligomerization is a process that can perform the conversion of C2-C5 olefins into more desirable products. More specifically, it can convert C2-C5 olefins into a diesel range product, or distillate. However, depending on the catalyst, the product from the oligomerization may have very poor diesel quality.

Jet fuel is one of the few petroleum fuels that cannot be replaced easily by electrical motor systems because a high energy output is required to fuel planes which cannot currently be supplied with electric motors. Large incentives are currently available for green jet fuel in certain regions.

An efficient process is desired for converting oxygenates to distillate fuels. More particularly, it is desirable to produce jet fuels having a higher cycloparaffin concentration due to their higher energy density, lower viscosity, better cold weather and combustion properties. When jet fuel is made from fossil fuels there are up to 25 wt % aromatic compounds in the fuel according to the specification. However, when fuels are made from a starting point of methanol or ethanol, there is a very low level of aromatic compounds present. This makes it necessary to blend the fuel with a fossil fuel derived portion in order to increase the aromatics level in the fuel. However, it would be desirable to be able to make a usable jet fuel from methanol or ethanol without the need to mix in a portion of a fossil fuel derived fuel.

BRIEF SUMMARY

The process involves the conversion of methanol to jet fuel where the fuel is a sustainable aviation fuel. This process is done by the conversion of methanol to olefins, followed by oligomerization and hydrogenation of olefins to produce the final jet fuel product. It is desirable to make a fuel that meets all of the specifications for jet fuel that are more stringent than for cycloparaffins and aromatics, 15 and 0.5% currently. It has been found that the modification of the olefin oligomerization steps can produce more aromatic compounds which then can be hydrogenated over a noble metal catalyst. The modifications in the process include the use of alkali modified ZSM-5, beta or Y-zeolite catalysts in the methanol to olefin process instead of SAPO-34 catalyst. A cofeed of small amounts of benzene or toluene to the methanol to olefin process may also facilitate the production of greater amounts of aromatics. A higher temperature such as in the range of 150-200° C. as compared to operating in the range of 80-140° C. in the oligomerization process when using a low Si/Al ratio ASA catalyst can produce a higher quantity of aromatic compounds. Any combination of modification of the methanol conversion or the oligomerization process may be employed in order to produce a jet fuel meeting the requirement of an increased amount of cycloolefins.

BRIEF DESCRIPTION OF THE DRAWINGS

FIG. 1 is a schematic drawing of a process and apparatus of the present disclosure.

DEFINITIONS

The term "communication" means that fluid flow is operatively permitted between enumerated components, which may be characterized as "fluid communication".

The term "downstream communication" means that at least a portion of fluid flowing to the subject in downstream communication may operatively flow from the object with which it fluidly communicates.

The term "upstream communication" means that at least a portion of the fluid flowing from the subject in upstream communication may operatively flow to the object with which it fluidly communicates.

The term "direct communication" means that fluid flow from the upstream component enters the downstream component without passing through any other intervening vessel.

The term "indirect communication" means that fluid flow from the upstream component enters the downstream component after passing through an intervening vessel.

The term "column" means a distillation column or columns for separating one or more components of different volatilities. Unless otherwise indicated, each column includes a condenser on an overhead of the column to condense and reflux a portion of an overhead stream back to the top of the column and a reboiler at a bottom of the column to vaporize and send a portion of a bottoms stream back to the bottom of the column. Feeds to the columns may be preheated. The top pressure is the pressure of the overhead vapor at the vapor outlet of the column. The bottom temperature is the liquid bottom outlet temperature. Overhead lines and bottoms lines refer to the net lines from the column downstream of any reflux or reboil to the column. Stripping columns may omit a reboiler at a bottom of the column and instead provide heating requirements and separation impetus from a fluidized inert media such as steam. Stripping columns typically feed a top tray and take main product from the bottom.

As used herein, the term "diesel" means hydrocarbons boiling in the range of an IBP between about 125° C. (257° F.) and about 175° C. (347° F.) or a T5 between about 150° C. (302° F.) and about 200° C. (392° F.) and the "diesel cut point" comprising a T95 between about 343° C. (650° F.) and about 399° C. (750° F.) using the TBP distillation method or a T90 between 280° C. (536° F.) and about 340° C. (644° F.) using ASTM D-86. The term "green diesel" means diesel comprising hydrocarbons not sourced from fossil fuels.

As used herein, the term "green hydrogen" is hydrogen produced from a non-fossil-fuel source, typically by a water hydrolysis unit.

As used herein, the term "T5", "T10", "T90" or "T95" means the temperature at which 5 percent by mass or volume, 10 percent by mass or volume, 90 percent by mass or volume or 95 percent by mass or volume, as the case may be, respectively, of the sample boils using ASTM D-86 or TBP.

As used herein, the term "end point" (EP) means the temperature at which the sample has all boiled off using ASTM D-7169, ASTM D-86 or TBP, as the case may be.

As used herein, the term "jet fuel" means hydrocarbons boiling in the range of a T10 between about 190° C. (374° F.) and about 215° C. (419° F.) and an end point of between about 290° C. (554° F.) and about 310° C. (590° F.). The term "green jet fuel" means jet fuel comprising hydrocarbons not sourced from fossil fuels.

As used herein, the term "predominant" or "predominate" means greater than 50%, suitably greater than 75% and preferably greater than 90%.

As used herein, the term "a component-rich stream" or "rich stream" means that the rich stream coming out of a vessel has a greater concentration of the component than the feed to the vessel and preferably than all other streams withdrawn from the vessel.

As used herein, the term "a component-lean stream" or "lean stream" means that the lean stream coming out of a vessel has a smaller concentration of the component than the feed to the vessel and preferably than all other streams withdrawn from the vessel.

As used herein, the term "rich" means greater than 50%, suitably greater than 75% and preferably greater than 90%.

As used herein, the term "separator" means a vessel which has an inlet and at least an overhead vapor outlet and a bottoms liquid outlet and may also have an aqueous stream outlet from a boot. A flash drum is a type of separator which may be in downstream communication with a separator that may be operated at higher pressure.

DETAILED DESCRIPTION

In the proposed disclosure, the overall process for converting oxygenates to distillate fuel can be divided into several steps: Production of methanol or dimethyl ether is not included in this disclosure but can be made from carbon dioxide and hydrogen in a process comprising water-gas shift and methanol synthesis reactions. Methanol or dimethyl ether may be converted by a MTO process to provide C2 to C6 olefins for the following steps. Ethanol can also be dehydrated to produce ethylene. The C2 to C6 olefins are oligomerized to C9+ distillate that include kerosene and diesel. A two-stage oligomerization process is employed, usually with different catalysts in the stages. The C8+ olefinic distillate may be hydrogenated and split into green jet and green diesel products to meet jet fuel specifications.

The process and apparatus may include an MTO section 6, an oligomerization section 50, an olefin recovery section 88 and a hydrogenation section 110. Beginning with the MTO section 6, the process may include charging an oxygenate stream 10 to a MTO reactor 12 and contacting the oxygenate stream with an MTO catalyst at MTO reaction conditions to convert oxygenates to olefins and water. The MTO reactor 12 may provide fluidized catalyst operating at fast fluidized conditions. The oxygenate may be methanol, dimethyl ether, ethanol or combinations thereof. Methanol may be derived from a water gas shift reaction of carbon dioxide with hydrogen.

The process and apparatus disclosed involves the production of a liquid fuel from carbon oxide and hydrogen. The process comprises reacting a mixture of carbon oxide and hydrogen to produce methanol, water, and a waste gas containing hydrogen, carbon monoxide, and dimethyl ether (DME). The methanol is contacted with an MTO catalyst and concentrated to produce one or more olefin streams and a waste gas containing hydrogen, carbon monoxide, and methane. The one or more olefin streams are oligomerized with one or more oligomerization catalysts to produce an oligomerized olefin stream comprising light to heavy olefins and a waste gas stream containing hydrogen, ethane, propane, and light olefins. The oligomerized olefin stream and, in some embodiments, a portion of the light olefins are reacted with hydrogen in the presence of a hydrogenation catalyst to produce jet fuel, diesel fuel, naphtha, and a waste gas stream containing hydrogen, propane, butane, and other light hydrocarbons. See FIG. 1.

The combination of the MTO, oligomerization, and hydrogenation processes as described above results in a very high (>75%) selectivity of jet fuel. However, the value of the byproducts, diesel, naphtha, and waste gases, will depend on whether they can be used effectively as fuels.

Methanol is converted into light olefin products in a methanol to olefin (MTO) process. Molecular sieves such as microporous crystalline zeolite and non-zeolitic catalysts, particularly silicoaluminophosphates (SAPO), are known to promote the conversion of oxygenates such as methanol to hydrocarbon mixtures, particularly hydrocarbon mixtures composed largely of light olefins. SAPO catalysts and their formulation are generally taught in U.S. Pat. Nos. 4,499,327 A, 10,358,394 and 10,384,986. Light olefins produced from the MTO process are concentrated in ethylene and propylene but include C4-C6 olefins. However, it has been found in the present disclosure that the use of some other catalysts, such as alkali modified ZSM-5, beta zeolite or Y-zeolite catalysts result in an increased production of aromatic compounds that can then be converted to cycloparaffins in the hydrogenation reactor. While it may be more effective to produce the higher quantities of aromatic compounds from the MTO process alternatively or in addition adjustments may be made to the downstream oligomerization process to produce the desired higher amounts of aromatic compounds as discussed later herein. An alternative or additional way to increase the amounts of aromatic compounds is to cofeed small amounts of benzene or toluene. In an embodiment, 0.5-15 wt % aromatic compounds are added to the feed to the methanol stream. Aromatics provide a higher amount of energy as do cycloparaffins have a higher energy density, lower viscosity, better in cold weather and better combustion properties.

The MTO reaction conditions include contact with a catalyst at a pressure greater than about 4 barg, suitably greater than about 5 barg, more suitably greater than about 7 barg, most suitably greater than about 6 barg, preferably greater than about 8 barg and more preferably greater than about 10 barg up to about 14 barg. The MTO reaction temperature should be between about 300 and about 475° C. and suitably be between about 350 and about 450° C. A weight hourly space velocity ("WHSV") in the MTO reactor is in the range of about 2 to about 15 $hr^{-1}$, with a WHSV in the range of about 3 to about 7 $hr^{-1}$, e.g., about 5 $hr^{-1}$, being preferred.

The MTO catalyst is separated from the olefin stream after the MTO reaction, stripped of hydrocarbons with an inert gas such as nitrogen or steam and transported to a regenerator 14 in line 16 in which air is contacted with the spent catalyst to burn coke from the MTO catalyst. The circulation rate to the regenerator is set so as to maintain an average coke on spent catalyst discharged from the reactor to the regenerator in line 16 below about 4.4 wt % and preferably less than 4 wt %.

The MTO reactor 12 generates a product olefin stream in line 20. The olefin stream in line 20 may be passed to a dewatering column 22 to cool and separate water from the olefin stream; neutralize acidic compounds and generate a dewatered olefin stream in line 24 with reduced water content, and a water stream in line 26 to pass water for further processing. The dewatering column 22 may comprise two columns. The water stream in line 26 may be further treated to separate further oxygenates that can be recycled to the MTO reactor 12. The dewatered olefin stream in line 24 may be compressed and passed to a dimethyl ether (DME) recovery unit 30, which separates a deoxygenated olefin stream in line 32 and a DME rich stream in line 34 by means of absorption columns. The DME rich stream in line 34 can be recycled to the MTO reactor 10 and converted to olefins over the MTO catalyst. The deoxygenated olefin stream in line 32 may be rich in C2-C6 olefins.

The deoxygenated olefin stream in line 32 is oligomerized with an oligomerization catalyst to produce an oligomerized olefin stream comprising C9+ olefins. If the olefin stream has substantial ethylene, it may be initially contacted with a dimerization catalyst to dimerize the ethylene to butenes and then contacted with oligomerization catalyst to oligomerize dimerized ethylene and un-dimerized higher olefins in the dimerized olefin stream to C9+ olefins in an embodiment. In other instances, the olefin stream is contacted first with the oligomerization catalyst and then the dimerization catalyst. The oligomerization catalyst that is used may be a nickel on amorphous silica-alumina that is operated at an elevated temperature of from 160-220 C (as compared to prior art temperatures of 80-150 C). The use of this catalyst at the higher temperature significantly favors production of cycloparaffins. In one example, 11 wt % cycloparaffins were produced at the higher temperatures as compared to 2.8 wt % at lower temperatures. In some instances, the ethylene is first passed over the zeolitic catalyst instead of the nickel containing catalyst. Herein the two stages of oligomerization will generally be referred to as a first stage and a second stage since dimerization may occur in either stage as may oligomerization.

The deoxygenated olefin stream in line 32 may be selectively hydrogenated to convert diolefins and acetylenes to monoolefins. Hydrogen may be added to the light olefin stream in line 36. The selective hydrogenation reactor 40 is normally operated at relatively mild hydrogenation conditions. The light olefin stream will normally be maintained under the minimum pressure sufficient to maintain the reactants as liquid phase hydrocarbons. A broad range of suitable operating pressures therefore extends from about 2.8 barg (40 psig) to about 55 barg (800 psig), or about 3.5 barg (50 psig) to about 21 barg (300 psig). A relatively moderate temperature between about 25° C. (77° F.) and about 350° C. (662° F.), or about 50° C. (122° F.) and about 200° C. (392° F.) is typically employed. The liquid hourly space velocity of the reactants through the selective hydrogenation catalyst should be above about 1.0 $hr^{-1}$ and about 35.0 $hr^{-1}$. To avoid the undesired saturation of a significant amount monoolefinic hydrocarbons, the mole ratio of hydrogen to diolefinic hydrocarbons in the material entering the bed of selective hydrogenation catalyst is maintained between about 0.75:1 and about 1.8:1.

Any suitable catalyst which is capable of selectively hydrogenating diolefins in a naphtha stream may be used. Suitable catalysts include, but are not limited to, a catalyst comprising copper and at least one other metal such as titanium, vanadium, chrome, manganese, cobalt, nickel, zinc, molybdenum, and cadmium or mixtures thereof. The metals are preferably supported on inorganic oxide supports such as silica and alumina, for example. The selectively hydrogenated olefin stream may exit the selective hydrogenation reactor in line 42 and enter a hydrogenation separator 44 to provide an overhead stream rich in hydrogen in line 46 that may be compressed, perhaps supplemented with a make-up hydrogen stream in line 47 and returned as recycle hydrogen in line 36. A selectively hydrogenated liquid, feed olefin stream from the bottom of the separator 44 may be transported to an oligomerization unit 50 in line 48. The feed olefin stream in line 48 may comprise at least 10 wt % ethylene, suitably at least 20 wt % ethylene and typically at least 25 wt % ethylene. The feed olefin stream in line 48 may predominantly comprise ethylene. The feed olefin stream may also comprise at least 10 wt %, suitably 20 wt % and typically 25 wt % of one or more of C3, C4, C5 and C6 olefins.

In other embodiments, the feed olefin stream in line 48 may predominantly comprise ethylene and be styled as an ethylene stream. In other embodiments, the feed olefin stream in line 48 may be a fresh olefin stream comprising ethylene and not originating from the MTO unit 6.

For example, the feed olefin stream may be provided from an ethanol dehydration process. Ethanol may be derived from any known thermal or biological process. Pure ethanol is not required, and aqueous ethanol may be used. For example, the concentration of ethanol may be between 20% and 100%. Ethanol or ethanol-containing feedstocks may be optionally fed to a dehydration reactor optionally with an inert gas such as nitrogen, pre-heated to a selected reaction temperature, and passed over a dehydration catalyst (e.g., alumina, modified alumina, silicoaluminate, modified silicoaluminate, and other catalysts) at a temperature and pressure sufficient to carry out the dehydration reaction that forms ethylene. Ethanol may be introduced to a dehydration reactor at a WHSV of between about 0.1 $hr^{-1}$ to about 30 $hr^{-1}$. In some embodiments, ethanol may be fed to the dehydration reactor at a WHSV of between about 0.5 $hr^{-1}$ to about 5 $hr^{-1}$. The dehydration reactor may be operated at a temperature from about 200° C. (392° F.) to about 500° C. (932° F.). In some embodiments, the dehydration reactor may be operated at a temperature from about 300° C. (572° F.) to about 450° C. (842° F.). In some embodiments, the dehydration reactor may be operated at a pressure from about 0 barg (0 psig) to about 83 barg (1203 psig). In some embodiments, the dehydration reactor may be operated at a pressure from about 0 barg (0 psig) to about 35 barg (507 psig). Ethanol conversion may vary depending on operating conditions and the selected catalyst from between about 10% and about 100%. The ethylene-containing product may be purified to remove water, by-products, oxygen, and other impurities. Purification could include condensing water and purifying the product through a purifying adsorbent such as silicas, molecular sieves, and carbons. The purified ethanol may be collected or passed directly to the oligomerization unit 50 as the feed olefin stream in line 48.

The oligomerization unit 50 may comprise a first stage oligomerization reactor 60 and a second stage oligomerization reactor 70. A light olefin splitter overhead line 106 transporting un-dimerized, recycle ethylene, a diluent stream comprising paraffins which may be a net stripped hydrogenated stream in line 148 and a dimerized recycle stream in line 52 comprising dimerized olefins may be added to the feed olefin stream in line 48 to provide a charge olefin stream in line 54. The charge olefin stream in line 54 may supply a primary charge olefin stream in line 56, and an interbed olefin charge stream in line 58. The primary charge olefin stream in line 56 may be heated and charged to the first stage oligomerization reactor 60. In an alternative embodiment, the first stage and second stage oligomerization reactors may be switched in position.

The diluent stream may comprise a paraffin stream that absorbs the exothermic heat generated by the oligomerization reaction. The diluent stream may be provided at a diluent-to-feed ratio of 1:1 to 6:1 and suitably 2:1 to 5:1. The diluent stream is preferably a C19+ paraffin stream, that may be taken from a stripper bottoms stream in line 146 downstream of hydrogenation. The diluent stream may also be a light paraffin stream.

The first stage oligomerization reactor preferably contains two fixed catalyst beds. The primary charge olefin stream is charged to the first catalyst bed in line 57 preferably in a down flow operation. However, upflow operation may be suitable. As dimerization of ethylene occurs in the first catalyst bed, an exotherm is generated. The interbed olefin charge stream is charged by line 58 into the reactor 60 at an interbed location to cool the dimerized effluent from the first bed. In an embodiment, the effluent from the first catalyst bed may be withdrawn from the first catalyst bed combined with interbed olefin charge stream in line 58, cooled in a heat exchanger such as a steam generator and returned to the second catalyst bed. Olefins exit the first stage oligomerization reactor 60 in line 64.

The first stage oligomerizaiton catalyst is preferably an amorphous silica-alumina base with a metal from either Group VIII and optionally Group VIB in the periodic table using Chemical Abstracts Service notations. In an aspect, the catalyst has a Group VIII metal promoted with a Group VIB metal. Typically, the silica and alumina will only be in the base, so the silica-to-alumina ratio will be the same for the catalyst as for the base. The metals can either be impregnated onto or ion exchanged with the silica-alumina base. Co-mulling is also contemplated. Additionally, a suitable catalyst will have a surface area of between about 50 and about 400 $m^2/g$ as determined by nitrogen BET.

The most preferred first stage oligomerization catalyst is prepared via a process where the mixing of raw materials to form a sol, the gelling and forming of the supports via dropping the sol into a hot oil bath and ageing of the gelled/formed supports are being conducted in an uninterrupted fashion. Such a process enables attainment of: (a) microscopically homogeneous silica-alumina composition through online intense mixing, (b) tight controls of shape and size of supports through the controls of the frequency of the vibrator and sizes of dropping tips and (c) surface areas, porosity and pore size distributions optimal for effective utilization of active sites, while minimizing side reactions. The raw materials comprise silicone and aluminum containing chemicals. In addition, a gelling reagent such as ammonia, urea or HMT (hexamethylenetetraamine) is incorporated. Once properly aged in an oil bath at atmospheric or elevated pressures, the spheres are transported to water wash tanks, where proper water wash can be applied to remove the unconverted materials. Optionally, the water wash can be conducted in the presence of ammonia or ammonium ions to remove alkali ions. Once washed, the wet spheres are transported to a drying apparatus to remove interstitial water and then to a calcination apparatus operating in a temperature range from about 450 to about 750° C. or preferably from 500 to 650° C. over a period from 1 to 24 hours at temperature. Optionally, various levels of steam can be injected into the calcination apparatus at a level of 5 to 100 vol % with the balance being nitrogen or air, and most preferably at a level of 10 to 80 vol %, to mitigate the tortuosity in the very small pores. The silica-to-alumina molar ratios of the supports range from about 0.8 to about 80 and most preferably range from about 5 to about 50. Most preferably the supports have silica-to-alumina molar ratios from about 5 to about 50 and having a tortuosity of less than about 5, preferably less than about 4 and most preferably less than about 3 and greater than about 1. It should be noted in this most preferable way of preparing the catalyst the elemental particles are packed in a homogeneous and orderly fashion, where the tortuosity is minimized.

Another suitable first stage oligomerization catalyst is described as follows. The suitable first stage oligomerization catalyst comprises an amorphous silica-alumina support. One of the components of the catalyst support utilized in the present invention is alumina. The alumina may be any of the various hydrous aluminum oxides or alumina gels such as alpha-alumina monohydrate of the boehmite or pseudo-boehmite structure, alpha-alumina trihydrate of the gibbsite structure, beta-alumina trihydrate of the bayerite structure, and the like. A particularly preferred alumina is available from Sasol North America Alumina Product Group under the trademark Catapal. This material is an extremely high purity alpha-alumina monohydrate (pseudo-boehmite) which after calcination at a high temperature has been shown to yield a high purity gamma-alumina. Another component of the catalyst support is an amorphous silica-alumina. Suitable silica-alumina has a silica-to-alumina molar ratio from about 0.8 to about 30, preferably 1.98 to 6.86, and can be synthesized using a batch or continuous process using a co-gel or sequential procedure with a balanced cation and anion, followed by aging, spray dry, and water wash. Proper ageing at pH of about 6 to bout 8 is preferred to attain pore textures with favorable mass transport properties.

Another component utilized in the preparation of the catalyst utilized in the present invention is a surfactant. The surfactant is preferably admixed with the hereinabove described alumina and the silica-alumina powders. The resulting admixture of surfactant, alumina and silica-alumina is then formed, dried and calcined as hereinafter described. The calcination effectively removes by combustion the organic components of the surfactant but only after the surfactant has dutifully performed its function in accordance with the present invention. Any suitable surfactant may be utilized in accordance with the present invention. A preferred surfactant is a surfactant selected from a series of commercial surfactants sold under the trademark "Antarox" by Solvay S. A. The Antarox surfactants are generally characterized as modified linear aliphatic polyethers and are low-foaming biodegradable detergents and wetting agents.

A suitable silica-alumina mixture is prepared by mixing proportionate volumes silica-alumina and alumina to achieve the desired silica-to-alumina ratio. In an embodiment, about 75 to about 95 wt-% amorphous silica-alumina with a silica-to-alumina ratio of about 2.6 to about 30 with about 10 to about 20 wt-% alumina powder will provide a suitable support. In an embodiment, other ratios of amorphous silica-alumina to alumina may be suitable.

Any convenient method may be used to incorporate a surfactant with the silica-alumina and alumina mixture. The surfactant is preferably admixed during the admixture and formation of the alumina and silica-alumina. A preferred method is to admix an aqueous solution of the surfactant with the blend of alumina and silica-alumina before the final formation of the support. It is preferred that the surfactant be present in the paste or dough in an amount from about 0.01 to about 10 wt-% based on the weight of the alumina and silica-alumina.

Monoprotic acid such as nitric acid or formic acid may be added to the mixture in aqueous solution to peptize the alumina in the binder. Additional water may be added to the mixture to provide sufficient wetness to constitute a dough with sufficient consistency to be extruded or spray dried.

The paste or dough may be prepared in the form of shaped particulates, with the preferred method being to extrude the dough mixture of alumina, silica-alumina, surfactant and water through a die having openings therein of desired size and shape, after which the extruded matter is broken into extrudates of desired length and dried. A further step of calcination may be employed to give added strength to the extrudate. Generally, calcination is conducted in a stream of dry air at a temperature from about 260° C. (500° F.) to about 815° C. (1500° F.).

The extruded particles may have any suitable cross-sectional shape, i.e., symmetrical or asymmetrical, but most often have a symmetrical cross-sectional shape, preferably a spherical, cylindrical or polylobal shape. The cross-sectional diameter of the particles may be as small as 40 μm; however, it is usually about 0.635 mm (0.25 inch) to about 12.7 mm (0.5 inch), preferably about 0.79 mm (1/32 inch) to about 6.35 mm (0.25 inch), and most preferably about 0.06 mm (1/24 inch) to about 4.23 mm (1/6 inch).

Typical characteristics of the amorphous silica-alumina supports utilized herein are a total pore volume, average pore diameter and surface area large enough to provide substantial space and area to deposit the active metal components. The total pore volume of the support, as measured by conventional mercury porosimeter methods, is usually about 0.2 to about 2.0 cc/gram, preferably about 0.25 to about 1.0 cc/gram and most preferably about 0.3 to about 0.9 cc/gram. Preferably, the amount of pore volume of the support in pores of diameter less than 40 Angstroms is less than about 0.10 cc/gram, preferably less than 0.15 cc/gram, and most preferably less than about 0.20 cc/gram. Surface area, as measured by the B.E.T. method, is typically above 50 $m^2$/gram, e.g., above about 200 $m^2$/gram, preferably at least 250 $m^2$/gram., and most preferably about 300 $m^2$/gram to about 400 $m^2$/gram.

To prepare the catalyst, the support material is compounded, as by a single impregnation or multiple impregnations of a calcined amorphous refractory oxide support particles, with one or more precursors of at least one metal component from Group VIII or VIB of the periodic table. The Group VIII metal, preferably nickel, should be present in a concentration of about 0.5 to about 15 wt-% and the Group VIB metal, preferably tungsten, should be present in a concentration of about 0 to about 12 wt-%. The impregnation may be accomplished by any method known in the art, as for example, by spray impregnation wherein a solution containing the metal precursors in dissolved form is sprayed onto the support particles. Another method is the multi-dip procedure wherein the support material is repeatedly contacted with the impregnating solution with or without intermittent drying. Yet other methods involve soaking the support in a large volume of the impregnation solution or circulating the support therein, and yet one more method is the pore volume or pore saturation technique wherein support particles are introduced into an impregnation solution of volume just sufficient to fill the pores of the support. On occasion, the pore saturation technique may be modified, so as to utilize an impregnation solution having a volume between 10 percent less and 10 percent more than that which will just fill the pores.

If the active metal precursors are incorporated by impregnation, a subsequent or second oxidation at elevated temperatures, as for example, between 399° C. (750° F.) and 760° C. (1400° F.), converts the metal precursors to their respective oxide forms. In some cases, calcinations may follow each impregnation of individual active metals. A subsequent calcination yields a catalyst containing the active metals in their respective oxide forms.

A preferred first stage oligomerization catalyst of the present invention has an amorphous silica-alumina base impregnated with 0.5-15 wt-% nickel in the form of 3.175 mm (0.125 inch) extrudates and a density of about 0.45 to about 0.65 g/ml. It is also contemplated that metals can be incorporated onto the support by other methods such as ion-exchange and co-mulling. In the preferred embodiment the catalyst has about 3 wt % nickel.

The charge olefin stream may be contacted with the first stage oligomerization catalyst at a temperature between about 60° C. (140° F.) to about 300° C. (572° F.). The reaction takes place predominantly in the gas phase at a LHSV 0.5 to 10 $hr^{-1}$ on an olefin basis. We have found that at least about 40 wt-% and as much as about 75 wt-% of the ethylene in the feed stream converts to higher olefins. The ethylene will initially dimerize over the catalyst to butenes.

The first stage oligomerization catalyst can be regenerated upon deactivation. Suitable regeneration conditions include subjecting the catalyst, for example, in situ, to hot air from about 450 to about 550° C. (842-1022° F.) for 3 hours. To facilitate regeneration without downtime, a swing bed arrangement is employed with an alternative first stage oligomerization reactor 60'. When first stage oligomerization catalyst in the first stage oligomerization reactor 60 is deactivated, valves on the primary charge line 57 and on the interbed charge line 58 to the first stage oligomerization reactor 60 are closed and valves on an alternative primary charge line 57' and on an alternative interbed charge line 58' are opened to charge the olefin stream to the alternative first stage oligomerization reactor 60'. A regeneration gas stream from line 62 is then admitted to the dimerization reactor 60 requiring regeneration. The regeneration gas may comprise air with an increased or decreased concentration of oxygen. The alternative first stage oligomerization reactor 60' can be regenerated in the reverse way by shutting the valves on line 57' and 58' and admitting regeneration gas from line 62'. Each first stage oligomerization reactor 60, 60' may include a vent line 63, 63', respectively, for exhausting regeneration flue gas. Activity and selectivity of the regenerated catalyst is comparable to fresh catalyst.

An olefin stream in line 66 is collected from lines 64 and 64' with an increased butene concentration compared to the charge olefin stream in line 54 and is split between a recycle stream in line 52 and a charge olefin stream in line 68. An intermediate olefin stream in a net light olefin splitter bottoms line 108 comprising C3-C8 olefins and an oligomerized recycle stream in line 72 comprising oligomerized olefins may be added to the charge olefin stream in line 68 to provide a charge oligomerization olefin stream in line 74. The charge oligomerization olefin stream in line 74 may be cooled and charged to the oligomerization reactor 70 in line 75. The second stage oligomerization reactor 70 may be in downstream communication with the first stage oligomerization reactor 60. The second stage oligomerization reactor 70 preferably operates in a down flow operation. However, upflow operation may be suitable. The charge oligomerization olefin stream is contacted with the second stage oligomerization catalyst causing the C2-C8 olefins to dimerize and trimerize to provide distillate range olefins. An oligomerized stream with an increased average carbon number greater than the charge oligomerization olefin stream in line 74 exits the second stage oligomerization reactor 70 in line 76.

The second stage oligomerization catalyst may include a zeolitic catalyst. The zeolite may comprise between about 5 and about 95 wt % of the catalyst, for example between about 5 and about 85 wt %. Suitable zeolites include zeolites having a structure from one of the following classes: MFI, MEL, ITH, IMF, TUN, FER, BEA, FAU, BPH, MEI, MSE, MWW, UZM-8, UZM-8HS, UZM-37, MOR, OFF, MTW, MRE, TON, MTT, MFS, AFO, ATO, and AEL. Three-letter codes indicating a zeotype are as defined by the Structure Commission of the International Zeolite Association and are maintained at http://www.iza-structure.org/databases. UZM-8 is as described in U.S. Pat. No. 6,756,030. In a preferred aspect, the second stage oligomerization catalyst may comprise a zeolite with a framework having a ten-ring pore structure. Examples of suitable zeolites having a ten-ring pore structure include MRE, TON, MTT, MFS, MFI, MEL, AFO, AEL, EUO and FER. In a further preferred aspect, the second stage oligomerization catalyst comprising a zeolite having a ten-ring pore structure may comprise a uni-dimensional pore structure. A uni-dimensional pore structure indicates zeolites containing non-intersecting pores that are substantially parallel to one of the axes of the crystal. The pores preferably extend through the zeolite crystal. Suitable examples of zeolites having a ten-ring uni-dimensional pore structure may include MTT. In a further aspect, the second stage oligomerization catalyst comprises an MTT zeolite. A suitable silica-to-alumina ratio of the MTT zeolite is about 30 to about 60.

The second stage oligomerization catalyst may be formed by combining the zeolite with a binder, and then forming the catalyst into pellets. The pellets may optionally be treated with a phosphorus reagent to create a zeolite having a phosphorous component between 0.5 and 15 wt % of the treated catalyst. The binder is used to confer hardness and strength on the catalyst. Binders include alumina, aluminum phosphate, silica, silica-alumina, zirconia, titania and combinations of these metal oxides, and other refractory oxides, and clays such as montmorillonite, kaolin, palygorskite, smectite and attapulgite. A preferred binder is an aluminum-based binder, such as alumina, aluminum phosphate, silica-alumina and clays.

One of the components of the catalyst binder utilized in the present invention is alumina. The alumina source may be any of the various hydrous aluminum oxides or alumina gels such as alpha-alumina monohydrate of the boehmite or pseudo-boehmite structure, alpha-alumina trihydrate of the gibbsite structure, beta-alumina trihydrate of the bayerite structure, and the like. A suitable alumina is available from UOP LLC under the trademark VERSAL. A preferred alumina is available from Sasol North America Alumina Product Group under the trademark Catapal. This material is an extremely high purity alpha-alumina monohydrate (pseudo-boehmite) which after calcination at a high temperature has been shown to yield a high purity gamma-alumina.

A suitable second stage oligomerization catalyst is prepared by mixing proportionate volumes of zeolite and alumina to achieve the desired zeolite-to-alumina ratio. In an embodiment, the zeolite content may contain about 5 to about 90, for example about 10 to about 85 wt % and suitably about 25 to about 75 wt % zeolite, and the balance alumina powder will provide a suitably supported catalyst. A silica support is also contemplated. In one exemplary embodiment, an MTT-type zeolite catalyst disposed on a high purity pseudo boehmite alumina substrate in a ratio of about 10/90 to about 90/10 and preferably between about 25/75 and about 75/25 is provided within the oligomerization reactor 70.

Monoprotic acid such as nitric acid or formic acid may be added to the mixture in aqueous solution to peptize the alumina in the binder. Additional water may be added to the mixture to provide sufficient wetness to constitute a dough with sufficient consistency to be extruded or spray dried. Extrusion aids such as cellulose ether powders can also be added. A preferred extrusion aid is available from The Dow Chemical Company under the trademark Methocel.

The paste or dough may be prepared in the form of shaped particulates, with the preferred method being to extrude the dough through a die having openings therein of desired size and shape, after which the extruded matter is broken into extrudates of desired length and dried. A further step of calcination may be employed to give added strength to the extrudate. Generally, calcination is conducted in a stream of air at a temperature from about 260° C. (500° F.) to about 815° C. (1500° F.). The MTT catalyst is not selectivated to neutralize acid sites such as with an amine.

The extruded particles may have any suitable cross-sectional shape, i.e., symmetrical or asymmetrical, but most often have a symmetrical cross-sectional shape, preferably a spherical, cylindrical or polylobal shape. The cross-sectional diameter of the particles may be as small as 40 μm; however, it is usually about 0.635 mm (0.25 inch) to about 12.7 mm (0.5 inch), preferably about 0.79 mm (1/32 inch) to about 6.35 mm (0.25 inch), and most preferably about 0.06 mm (1/24 inch) to about 4.23 mm (1/6 inch).

With regard to the second stage oligomerization reactor 70, process conditions are selected to produce a higher percentage of jet range olefins which, when hydrogenated in a subsequent step as will be described below, result in a desirable jet-range hydrocarbon product. In one exemplary embodiment, a zeolite catalyst disposed on an alumina substrate is provided within the second stage oligomerization reactor 70. The charge dimerized olefin stream in line 74 is cooled and charged to the second stage oligomerization reactor 70. To achieve the most desirable olefin product, the second stage oligomerization reactor 70 is run at a temperature from about 100° C. (212° F.) to about 270° C. (518° F.), and more preferably from about 111° C. (232° F.) to about 230° C. (446° F.). In order to produce the higher quantities of cycloparaffins that are sought, the temperature may range from 180-250° C. (356-482° F.) and preferably from 200-250° C. (392-482° F.). The second stage oligomerization reactor 70 is run at a pressure from about 21 barg (300 psig) to about 69 barg (1000 psig), and more preferably from about 49 barg (710 psig) to about 63 barg (900 psig). The nickel on alumina catalyst may be used in either the first stage or the second stage of the oligomerization reactor. It is important that the process be at the higher temperature in order to produce the desired amounts of cycloparaffins which may range from 5-30 wt %, 20-30 wt %, 25-30 wt % of the product stream after oligomerization and hydrogenation.

When the oligomerization reaction is performed according to the above-noted process conditions, a C4 olefin conversion of greater than or equal to about 95% is achieved, or greater than or equal to 97%. The resulting oligomerized olefin stream in line 76 includes a plurality of olefin products that are distillate range hydrocarbons. Under the conditions run to increase the production of cycloparaffins, at least 50% more cycloparaffins are produced.

The second stage oligomerization catalyst can be regenerated upon deactivation. Suitable regeneration conditions include subjecting the oligomerization catalyst, for example, in situ, to hot air at 500° C. (932° F.) for 3 hours. To facilitate regeneration without downtime, a swing bed arrangement is employed with an alternative dimerization reactor 70'. When the second stage oligomerization reactor 70 is deactivated, valves on the cooled charge line 75 to the second stage oligomerization reactor 70 are closed and valves on an alternative cooled charge line 75' are opened to charge the olefin stream to the alternative oligomerization reactor 70'. A regeneration gas stream from line 78 is then admitted to the second stage oligomerization reactor 70 requiring regeneration. The regeneration gas may comprise air with an increased or decreased concentration of oxygen. The alternative second stage oligomerization reactor 70' can be regenerated in the reverse way by shutting the valves on line 75' and admitting regeneration gas from line 78'. Each second stage oligomerization reactor 70, 70' may include a vent line 73, 73', respectively, for exhausting regeneration flue gas. Activity and selectivity of the regenerated catalyst is comparable to fresh catalyst. In other embodiments, the second stage oligomerization (zeolitic) catalyst is in the first position and the dimerization (Ni) catalyst is in the second position.

An oligomerized olefin stream in line 80 collected from lines 76, 76' with an increased C9+ olefin concentration compared to the charge oligomerization olefin stream in line 74 is split between an oligomerized recycle stream in line 72 and an oligomerized product stream in line 84.

The oligomerized product stream from the oligomerization unit 50 is conveyed to the olefin recovery section 88 in which it is fed to a heavy olefin splitter column 90. In the heavy olefin splitter column 90 oligomers that boil lower than the jet range hydrocarbons, typically C8-hydrocarbons with atmospheric boiling points less than about 150° C. (356° F.), are separated in a net heavy olefin splitter overhead stream in line 92 from a net heavy olefin splitter bottoms stream in line 94 comprising distillate-range C9+ hydrocarbons, typically C9-C20 olefins. The heavy olefin splitter column 90 may be operated at a bottoms temperature of about 300° C. (572° F.) to about 500° C. (932° F.) and an overhead pressure of about 9 barg to about 15 barg. The heavy olefin splitter overhead stream may be condensed and taken as a net vapor overhead from the heavy olefin splitter receiver 96 in line 92.

The C8- net vapor heavy olefin splitter overhead stream in line 92 may be fed to a light olefin splitter column 100. The light olefin splitter overhead stream may be chilled and separated in a light olefin splitter overhead receiver 102 into a net vapor overhead stream in line 104 comprising methane and lighter off gases and a net liquid light olefin splitter overhead stream in line 106 comprising ethylene. The net liquid light olefin splitter overhead stream in line 106 may recycle un-dimerized ethylene to the feed olefin stream in line 48 along with the diluent stream in line 148 and the dimerized recycle stream in line 52 to provide the charge olefin stream in line 54 to the first stage oligomerization reactor 60. The net liquid light olefin splitter overhead stream may predominantly comprise ethylene that can be recycled to the first stage oligomerization reactor 60. An intermediate olefin stream in a net light olefin splitter bottoms line 108 comprising C3-C8 olefins may be recycled to join the charge olefin stream in line 68 along with the oligomerized recycle stream in line 72 to provide the charge oligomerization olefin stream in line 74 to be oligomerized in the second stage oligomerization reactor 70. Drag streams may be taken from lines 106 and lines 108. The light olefin splitter column 100 may be operated at a bottoms temperature of about 100° C. (212° F.) to about 300° C. (572° F.) and an overhead pressure of about 5 barg to about 11 barg.

The net heavy olefin splitter bottoms stream in line 94 comprising distillate-range C9+ olefins may be hydrogenated to provide motor fuels to saturate the olefinic bonds in a hydrogenation reactor 120. This step is performed to ensure the product motor fuel meets or exceeds the thermal oxidation requirements specified in ASTM D7566-10a for hydroprocessed synthesized paraffinic kerosene (SPK) and applicable requirements for diesel. Hydrogenation is typically performed using a conventional hydrogenation or hydrotreating catalyst, and can include metallic catalysts containing, e.g., palladium, rhodium, nickel, ruthenium, platinum, rhenium, cobalt, molybdenum, or combinations thereof, and the supported versions thereof. Catalyst supports can be any solid, inert substance including, but not limited to, oxides such as silica, alumina, titania, calcium carbonate, barium sulfate, and carbons. The catalyst support can be in the form of powder, granules, pellets, or the like. A stream of hydrogen is provided in line 122 as the source for hydrogen to the hydrogenation reactor 120.

In an exemplary embodiment, hydrogenation is performed in the hydrogenation reactor 120 that includes a platinum-on-alumina catalyst, for example about 0.5 wt % to about 0.9 wt % platinum-on-alumina catalyst. Using this catalyst, hydrogenation suitably occurs at a temperature of about 125 (257° F.) to about 175° C. (347° F.) and at a pressure of about 35 barg (500 psig) to about 105 barg (1500 psig). According to these process conditions, the hydrogenation reactor 120 converts the olefins into a paraffin product having the same carbon number distribution as the olefins, thereby forming distillate-range paraffins suitable for use as jet and diesel fuel.

The hydrogenated distillate stream discharged from the hydrogenation reactor 120 in line 124 may be cooled and fed to a hydrogenation separator 130. In the hydrogenation separator 130, the hydrogenated distillate stream is separated into a hydrogenated separator vapor stream in an overhead line 132 and a hydrogenated separator liquid stream in a bottoms line 134. The hydrogenated separator vapor stream in line 132 may be compressed and combined with make-up hydrogen in line 136 to provide the hydrogen stream in line 122 and/or the hydrogen stream in line 36 for the selective hydrogenation reactor 40. The hydrogenated separator liquid stream in the bottoms line 134 may be heated by heat exchange with the hydrogenated distillate stream in line 124 and fed to a stripper column 140.

The stripper column 140 strips light gases from the hydrogenated separator liquid stream to provide a stripper off gas stream in off gas line 142 from a stripper overhead receiver 144. A net stripped hydrogenated stream in a stripper bottoms line 146 is split between a product fuel stream in line 147 and a diluent stream in line 148. The diluent stream in line 148 can be recycled to the feed olefin stream in line 48 along with light olefin splitter overhead stream 106 and the dimerized recycle stream in line 52 to provide the charge olefin stream in line 54. The diluent stream is inert in an oligomerization reactor and serves to absorb the exotherm in the first stage oligomerzation reactors 60, 60' and second stage oligomerization reactors 70, 70'. The stripper column 140 may be operated at a bottoms temperature of about 250° C. (482° F.) to about 500° C. (932° F.) and an overhead pressure of about 2 barg to about 8 barg.

The product fuel stream in line 147 may be fed to the jet fractionation column 150 to be separated into an off-gas stream in an overhead line 152 from a jet receiver overhead 154, a green jet fuel stream from the jet receiver bottoms line 156 and a green diesel stream in the net diesel bottoms line 158. Both the jet fuel stream in line 156 and the diesel stream in line 158 can be fed to their respective fuel pools. The jet fractionation column 150 may be operated at a bottoms temperature of about 350° C. (662° F.) to about 600° C. (1112° F.) and an overhead pressure of about 1 barg to about 5 barg.

EXAMPLES

Example 1

In this Example as shown in Table 1, 17.3 wt. % cycloparaffins were produced.

TABLE 1

| | 2nd stage oligomerization | 1st stage oligomerization |
|---|---|---|
| Catalyst | 3% Ni/DHC-8 | 75% MTT/V-251 |
| Inlet Temperature (° C.) | 200 | 250 |
| Pressure (psig) | 900 | 900 |
| Jet effluent composition after hydrogenation and fractionation | | |
| n-paraffins, wt % | 3.5 | |
| isoparaffins, wt % | 79.2 | |
| olefins, wt % | 0 | |
| cyclo-paraffins, wt % | 17.3 | |
| 1-R aromatics, wt % | 0 | |

Example 2

$1^{st}$ and $2^{nd}$ stage oligomerization can optionally be reversed as shown in the following data in Table 2.

TABLE 2

| | 2nd stage oligomerization | 1st stage oligomerization |
|---|---|---|
| Catalyst | 3% Ni/DHC-8 | 25% MTT/V-251 |
| Inlet Temperature (° C.) | 160+ | 200-240 |
| Pressure (psig) | 900 | 900 |
| Jet effluent composition after hydrogenation and fractionation | | |
| n-paraffins, wt % | 7 | |
| isoparaffins, wt % | 82 | |
| olefins, wt % | 0 | |
| cyclo-paraffins, wt % | 11 | |
| 1-R aromatics, wt % | 0 | |

Example 3

Example 3 shows that with a lower temperature at the inlet that significantly less cycoparaffins are produced.

TABLE 3

| | 2nd stage oligomerization | 1st stage oligomerization |
|---|---|---|
| Catalyst | 3% Ni/DHC-8 | 25% MTT/V-251 |
| Inlet Temperature (° C.) | 80 | 250 |
| Pressure (psig) | 900 | 900 |
| Jet effluent composition after hydrogenation and fractionation | | |
| n-paraffins, wt % | 0.5 | |
| isoparaffins, wt % | 96.6 | |
| olefins, wt % | 0 | |
| cyclo-paraffins, wt % | 2.8 | |
| 1-R aromatics, wt % | 0 | |

Specific Embodiments

While the following is described in conjunction with specific embodiments, it will be understood that this description is intended to illustrate and not limit the scope of the preceding description and the appended claims.

A first embodiment of the present disclosure is a process for increased production of cycloparaffins, said process comprising contacting a methanol stream with a catalyst comprising an alkali modified ZSM-5, beta or Y-zeolite to produce an olefin stream, oligomerizing said olefin stream in a two-stage oligomerization process under conditions to produce an effluent containing an increased amount of cycloolefins and then hydrogenating said effluent to produce a product stream containing an increased amount of cycloparaffin compounds. An embodiment of the present disclosure is one, any or all of prior embodiments in this paragraph up through the first embodiment in this paragraph wherein said two-stage oligomerization process comprises a first stage oligomerization process and a second stage oligomerization process. An embodiment of the present disclosure is one, any or all of prior embodiments in this paragraph up through the first embodiment in this paragraph wherein said two-stage oligomerization process comprises a first stage oligomerization process and a second stage oligomerization process. An embodiment of the present disclosure is one, any or all of prior embodiments in this paragraph up through the first embodiment in this paragraph wherein an ethanol stream is contacted with a catalyst comprising an alumina-based catalyst to produce an olefin stream. An embodiment of the present disclosure is one, any or all of prior embodiments in this paragraph up through the first embodiment in this paragraph wherein the olefin stream comprises ethylene and propylene. An embodiment of the present disclosure is one, any or all of prior embodiments in this paragraph up through the first embodiment in this paragraph wherein the olefin stream comprises ethylene, wherein the amount of cycloparaffins compounds produced in said product stream after hydrogenation is about 5 to 30 wt %. An embodiment of the present disclosure is one, any or all of prior embodiments in this paragraph up through the first embodiment in this paragraph wherein said two-stage oligomerization process produces said effluent comprising about 5 to 30 wt % cycloolefin and aromatic compounds. An embodiment of the present disclosure is one, any or all of prior embodiments in this paragraph up through the first embodiment in this paragraph wherein in one of the two stages of said oligomerization process an oligomerization reactor contains an oligomerization catalyst comprises a metal on an amorphous silica alumina base. An embodiment of the present disclosure is one, any or all of prior embodiments in this paragraph up through the first embodiment in this paragraph wherein the metal comprises nickel, wherein said catalyst comprises about 3% nickel. An embodiment of the present disclosure is one, any or all of prior embodiments in this paragraph up through the first embodiment in this paragraph wherein said nickel on amorphous silica alumina catalyst is in the second stage of said oligomerization process. An embodiment of the present disclosure is one, any or all of prior embodiments in this paragraph up through the first embodiment in this paragraph wherein said the amorphous silica alumina in the oligomerization catalyst has a Si/Al ratio of from 1.98 to 6.86. An embodiment of the present disclosure is one, any or all of prior embodiments in this paragraph up through the first embodiment in this paragraph wherein said olefin contacts said nickel on amorphous silica alumina oligomerization catalyst at a temperature from about 150-200° C. An embodiment of the present disclosure is one, any or all of prior embodiments in this paragraph up through the first embodiment in this paragraph wherein in a second of the two stages of said oligomerization process, an oligomerization reactor contains an oligomerization catalyst comprising an acidic catalyst. An embodiment of the present disclosure is one, any or all of prior embodiments in this paragraph up through the first embodiment in this paragraph wherein the acidic catalyst comprises a zeolite. An embodiment of the present disclosure is one, any or all of prior embodiments in this paragraph up through the first embodiment in this paragraph wherein said olefin contacts said acidic oligomerization catalyst at a temperature from about 190-250° C. An embodiment of the present disclosure is one, any or all of prior embodiments in this paragraph up through the first embodiment in this paragraph further comprising adding 0.5-15 wt % aromatic compounds to the feed to the methanol stream.

Without further elaboration, it is believed that using the preceding description that one skilled in the art can utilize the present disclosure to its fullest extent and easily ascertain the essential characteristics of this disclosure, without departing from the spirit and scope thereof, to make various changes and modifications of the disclosure and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for increased production of cycloparaffins, said process comprising contacting a methanol stream with a catalyst comprising an alkali modified ZSM-5, a beta zeolite, or a Y-zeolite to produce an olefin stream, oligomerizing said olefin stream in a two-stage oligomerization process under conditions to produce an effluent containing an increased amount of cycloolefins and then hydrogenating said effluent to produce a product stream containing an increased amount of cycloparaffin compounds, wherein the amount of cycloparaffins compounds produced in said product stream after hydrogenation is about 5 to 30 wt %.

2. The process of claim 1 wherein said two-stage oligomerization process comprises a first stage oligomerization process and a second stage oligomerization process.

3. The process of claim 1, wherein said process further comprises contacting an ethanol stream with a catalyst comprising an alumina-based catalyst to produce an olefin stream.

4. The process of claim 1, wherein the olefin stream comprises ethylene and propylene.

5. The process of claim 3, wherein the olefin stream comprises ethylene.

6. The process of claim 1 wherein said two-stage oligomerization process produces said effluent comprising about 5 to 30 wt % cycloolefin and aromatic compounds.

7. The process of claim 1 wherein in one of the two stages of said oligomerization process an oligomerization reactor contains an oligomerization catalyst comprises a metal on an amorphous silica alumina base.

8. The process of claim 7 wherein the metal comprises nickel.

9. The process of claim 8 wherein said catalyst comprises about 3% nickel.

10. The process of claim 3 wherein said nickel on amorphous silica alumina catalyst is in the second stage of said oligomerization process.

11. The process of claim 7 wherein said the amorphous silica alumina in the oligomerization catalyst has a Si/Al ratio of from 1.98 to 6.86.

12. The process of claim 1 wherein said olefin contacts said nickel on amorphous silica alumina oligomerization catalyst at a temperature from about 150-200° C.

13. The process of claim 1 wherein in a second of the two stages of said oligomerization process, an oligomerization reactor contains an oligomerization catalyst comprising an acidic catalyst.

14. The process of claim 13 wherein the acidic catalyst comprises a zeolite.

15. The process of claim 13 wherein said olefin contacts said acidic oligomerization catalyst at a temperature from about 190-250° C.

16. The process of claim 1 further comprising adding 0.5-15 wt % aromatic compounds to the feed to the methanol stream.

* * * * *